(12) United States Patent
Grenda et al.

(10) Patent No.: US 6,827,971 B2
(45) Date of Patent: Dec. 7, 2004

(54) USE OF POLYURETHANE POWDER COATING MATERIALS

(75) Inventors: Werner Grenda, Herne (DE); Andreas Wenning, Nottuln (DE)

(73) Assignee: Degussa AG, Duesseldorf (DE)

( * ) Notice: Subject to any disclaimer, the term of this patent is extended or adjusted under 35 U.S.C. 154(b) by 96 days.

(21) Appl. No.: 10/309,894

(22) Filed: Dec. 5, 2002

(65) Prior Publication Data

US 2003/0104181 A1 Jun. 5, 2003

(30) Foreign Application Priority Data

Dec. 5, 2001 (DE) .......................... 101 59 768

(51) Int. Cl.[7] .................................. B05D 3/02
(52) U.S. Cl. .................... 427/195; 427/388.2
(58) Field of Search ................ 427/180, 189, 427/195, 388.1, 388.2

(56) References Cited

U.S. PATENT DOCUMENTS

| 3,822,240 A | | 7/1974 | Schmitt et al. |
| 3,931,117 A | | 1/1976 | Leonard |
| 4,246,132 A | * | 1/1981 | Gras et al. ............. 252/182.22 |
| 4,246,380 A | | 1/1981 | Gras et al. |
| 4,404,320 A | | 9/1983 | Goto et al. |
| 4,419,513 A | * | 12/1983 | Breidenbach et al. ....... 544/222 |
| 4,500,697 A | * | 2/1985 | Disteldorf et al. ............ 528/45 |
| 5,331,078 A | | 7/1994 | Gras et al. |
| 5,384,358 A | | 1/1995 | Wamprecht et al. |

FOREIGN PATENT DOCUMENTS

| DE | 2 166 423 | | 1/1974 |
| DE | 4338265 | * | 12/1994 |
| DE | 19729242 | * | 1/1999 |
| EP | 0 512 213 | | 11/1992 |
| WO | WO 97 / 47400 | * | 12/1997 |

* cited by examiner

*Primary Examiner*—Erma Cameron
(74) *Attorney, Agent, or Firm*—Oblon, Spivak, McClelland, Maier & Neustadt, P.C.

(57) ABSTRACT

The use of pulverulent thermosetting coating compositions based on physical mixtures of individual isocyanato isocyanurates formed from aliphatic and (cyclo)aliphatic and/or cycloaliphatic diisocyanates and from polyesters containing hydroxyl groups and terephthalic acid for coil powder coating materials, to a process for producing such coatings, and to the metal coils coated with such coating materials.

19 Claims, No Drawings

USE OF POLYURETHANE POWDER COATING MATERIALS

BACKGROUND OF THE INVENTION

1. Field of the Invention

The present invention relates to the use of pulverulent thermosetting coating compositions based on physical mixtures of individual isocyanato isocyanurates formed from aliphatic and (cyclo)aliphatic and/or cycloaliphatic diisocyanates and from polyesters containing hydroxyl groups and terephthalic acid for coil powder coating materials, to a process for producing such coatings, and to the metal coils coated with such coating materials.

2. Description of the Background

Thermosetting powder coating compositions are used intensively for producing crosslinked coatings on a wide variety of substrates. Thermosetting coatings are generally harder than thermoplastic compositions, are more resistant to solvents and detergents, possess better adhesion to metallic substrates, and do not soften on exposure to increased temperatures.

Since 1970, thermosetting pulverulent materials have been known which are obtained by reacting a hydroxyl-containing resin with a blocked polyisocyanate. Of the blocked polyisocyanates, isophorone diisocyanate adducts blocked with $\epsilon$-caprolactam have become established as curatives for PU powders. The PU powders prepared using these curatives are employed for coating a wide variety of articles made of metal, on account of their superior weathering stability and thermal color stability. Powders of this kind are described, for example, in DE 27 35 497. Using these powders, ready-formed metal components are coated piece by piece (post-coated metal).

Coil coating, on the other hand, is a process for coating metal coils at speeds from 60 to 200 m/min. Metal sheets, preferably of steel or aluminum, are cleaned and coated with a paint. These metal sheets are then passed on for further processing, where they acquire their actual form. The principal applications are trapezoidal profiles coated with weather-resistant paints, for roofs and facings of buildings, for example, and also doors, window frames, gates, guttering, and blinds. For the interior, coil-coated metal sheets are employed primarily for partition walls and ceiling elements. Other fields of use include steel furniture, shelving, shopfitting, and appliance casings. Lamps and light fittings form a further important application segment. There is also a broad applications pallet in the vehicle segment. Truck bodies and exterior-mounted automotive components are often manufactured from precoated materials.

For coating the substrate used, a pretreatment is generally conducted. As the first coating film, a primer is applied in a thickness of from 5 to 10 $\mu$m to what will subsequently be the visible side. Following the first pass through the dryer, the actual topcoat is applied. After drying it has a film thickness of approximately 20 $\mu$m. In some cases this surface is further laminated, while hot, with a temporary protective sheet. This is intended to protect it against mechanical injury. In parallel with the coating of the visible sides, the reverse sides as well are coated. Primers used include, for example polyester resins. For coil-coated facings and roofs under corrosive industrial atmospheric conditions, epoxy-containing systems are used as primers. As topcoat materials, liquid coating materials in innumerable colors are used primarily. Depending on the field of application, polyester, polyurethane or PVDF topcoat materials, for example, are employed. The film thicknesses of the topcoats are normally about 20 $\mu$m.

Besides the liquid primers and topcoats, powder coating materials are also used for the coil coating of metal coils. Powder coating materials have the great advantage over their liquid counterparts of being solvent-free and hence more ecological. However, their proportion among the coil coating systems has to date been relatively low.

One of the reasons was the high powder coating film thickness of more than 40 $\mu$m. This leads to optical defects, since the surface is no longer entirely free from pores. This drawback was eliminated by WO 97/47400. It describes a process for coating metal coils, with which powder film thicknesses of less than 20 $\mu$m can be obtained.

A second disadvantage as compared with liquid coating materials was the extremely slow coil speed during application of the powder coating material. Using electrostatic spray guns, metal coils can be coated with powder coating material only at line speeds of a maximum of 20 m/min. As a result of the MSC Powder Cloud™ technology, described, for example, by F. D. Graziano, XXIIIrd International Conference in Organic Coatings, Athens, 1997, pages 139–150 or by M. Kretschmer, 6th DFO Conference on Powder Coating Practice, Dresden, 2000, pages 95–100, coil speeds of from 60 to 100 m/min are now realizable.

PU powder coating materials are known, inter alia, for their high weathering stability, excellent leveling, and good flexibility. For use in coil coating, however, the flexibility of the systems known to date is often inadequate. Consequently, the search is on for new PU powder coating materials which satisfy the extreme flexibility requirement of coil coatings. Success in this search, if achieved, would remove the third critical disadvantage relative to conventional liquid coating materials.

EP 0 047 452 describes isocyanato isocyanurates, based on hexamethylene diisocyanate or isophorone diisocyanate, which following blocking of the NCO groups can be used as crosslinkers for producing flexible solvent-borne or pulverulent polyurethane coatings.

EP 0 132 518 describes a composition which is based on polyhydroxy components and trimers of 2-methylpentyl 1,5-diisocyanate, 2-ethylbutane 1,4-diisocyanate, and isophorone diisocyanate and which is a suitable binder for powder coating materials for the coating of heat-curable substrates.

DE 197 29 242 describes pulverulent binders comprising a hydroxyl-containing polyacrylate and physical mixtures of at least one aliphatic isocyanate component containing isocyanurate or urethane or biuret groups and at least one (cyclo)aliphatic isocyanate component containing isocyanurate and/or urethane groups and/or cycloaliphatic isocyanate component containing isocyanurate and/or urethane groups, whose NCO groups are blocked with $\epsilon$-caprolactam.

The powder coating materials described in the aforementioned prior art are used exclusively for coating metal preforms. Their use for coating in accordance with the coil coating processes is not described.

SUMMARY OF THE INVENTION

Surprisingly it has been found that a selection of certain crosslinkers from those described above with certain hydroxyl-containing polyesters may be processed to binders which are suitable for coating metallic substrates by the coil coating process.

The invention accordingly provides for the use of polyurethane powder coating materials for coating metal coils by the coil coating process, wherein said materials comprise A) an isocyanate component which is totally or partly blocked with ε-caprolactam and comprises physical mixtures of individual isocyanato isocyanurates of aliphatic and (cyclo)aliphatic and/or cycloaliphatic diisocyanates, B) polyesters containing hydroxyl groups and terephthalic acid, and C) if desired, customary auxiliaries and additives, and where there are 0.5–1.2 NCO groups of component A) per OH group of component B).

Thus, the present invention includes a process for coating metal coils, comprising:

coil coating a metal coil with a polyurethane powder coating material which is the reaction product of A) an isocyanate component which is totally or partly blocked with ε-caprolactam and comprises physical mixtures of individual isocyanato isocyanurates of aliphatic and (cyclo)aliphatic and/or cycloaliphatic diisocyanates, and B) one or more polyesters containing hydroxyl groups and terephthalic acid, and wherein there are 0.5–1.2 NCO groups of A) per OH group of B).

The invention further provides metal coils coated with polyurethane powder coating materials by the coil coating process, wherein the polyurethane powder coating materials comprise A) an isocyanate component which is totally or partly blocked with ε-caprolactam and comprises physical mixtures of individual isocyanato isocyanurates of aliphatic and (cyclo)aliphatic and/or cycloaliphatic diisocyanates, B) polyesters containing hydroxyl groups and terephthalic acid, and C) if desired, customary auxiliaries and additives, and where there are 0.5–1.2 NCO groups of component A) per OH group of component B).

A more complete appreciation of the invention and many of the attendant advantages thereof will be readily obtained as the same becomes better understood by reference to the following detailed description.

DETAILED DESCRIPTION OF THE INVENTION

Starting compounds used for preparing isocyanate component A) are the isocyanato isocyanurates of diisocyanates of aliphatic and (cyclo)aliphatic and/or cycloaliphatic structure. By (cyclo)aliphatic diisocyanates the skilled worker understands NCO groups which are at the same time attached adequately both cyclically and aliphatically, as is the case for isophorone diisocyanate, for example. Cycloaliphatic diisocyanates, in contrast, are those which have only NCO groups attached directly to the cycloaliphatic ring. Diisocyanates of this kind are described, for example, in Houben-Weyl, Methoden der organischen Chemie, Volume 14/2, p. 61 ff. and J. Liebigs Annalen der Chemie, Volume 526, pp. 75–136, each of which is incorporated herein by reference. Preference is generally given to using the aliphatic diisocyanates which are easy to obtain industrially, such as hexamethylene diisocyanate, 2-methylpentamethylene 1,5-diisocyanate, 2-ethyltetramethylene 1,4-diisocyanate or trimethylhexamethylene 1,6-diisocyanate, especially the 2,2,4 and the 2,4,4 isomer and technical-grade mixtures of both isomers, the (cyclo)aliphatic diisocyanates such as isophorone diisocyanate, and the cycloaliphatic diisocyanates such as 4,4'-diisocyanatodicyclohexylmethane or norbornane diisocyanate.

The isocyanato isocyanurates are prepared conventionally as specified in GB 13 91 066, DE 23 25 826, DE 26 44 684 or DE 29 16 201, each of which is incorporated herein by reference. The process products are composed of isocyanato isocyanurate (trimer) with higher oligomers where appropriate. They have a total NCO content of from 8 to 22% by weight. This range for the NCO content includes all specific values and subranges therebetween, such as 10, 12, 14, 16, 18, and 20% by weight.

The isocyanate component A) employed in accordance with the invention is always composed of a physical mixture of at least one aliphatic isocyanato isocyanurate and at least one representative from the group consisting of (cyclo) aliphatic and cycloaliphatic isocyanato isocyanurates.

The ratio of the isocyanato isocyanurates of aliphatic diisocyanates to the sum of (cyclo)aliphatic and/or cycloaliphatic diisocyanates varies preferably from 70:30% by weight to 30:70% by weight. This range includes all specific values and subranges therebetween, such as 65:35, 60:40, 55:45, 40:60, and 35:65% by weight.

For carrying out the blocking reaction, the isocyanato isocyanurates are generally introduced as an initial charge and the ε-caprolactam blocking agent is added in portions. The reaction may be carried out without solvent or else in the presence of suitable (inert) solvents. It is preferred, however, to operate without solvent. The isocyanato isocyanurate mixture is heated to 90–130° C. At this temperature, the blocking agent is added conventionally. After the end of the addition of the blocking agent, the reaction is completed by heating of the reaction mixture at 120° C. for about 1 to 2 hours. The blocking agent is added in amounts such that from 0.5 to 1.1 mol of blocking agent, preferably from 0.8 to 1 mol, with particular preference 1 mol, are reacted per NCO equivalent of the isocyanato isocyanurate mixture. In order to accelerate the isocyanate polyaddition reaction it is possible to add the catalysts which are customary in polyurethane chemistry, such as organic tin compounds, zinc compounds or amine compounds, for example, in an amount of from 0.01 to 1% by weight, based on the total mixture.

The solvent-free blocking reaction may also be conducted continuously in a static mixer or advantageously in a multiscrew kneading apparatus, particularly in a twin-screw extruder.

The total NCO content of the isocyanate component blocked totally or partially with ε-caprolactam is from 8 to 22% by weight, preferably from 9 to 16% by weight.

The coating composition used in accordance with the invention is prepared using polyesters containing hydroxyl groups and terephthalic acid.

The polyesters B) containing hydroxyl groups and terephthalic acid that are to be used have an OH functionality of from 2.0 to 5, preferably from 2.5 to 4.2, a number-average molecular weight of from 800 to 8 000, preferably from 1 200 to 5 000, an OH number of from 20 to 200 mg KOH/g, preferably from 30 to 100 mg KOH/g, a viscosity at 160° C. of <80 000 mPa·s, preferably <60 000 mpa·s, and a melting point of ≧70° C. to ≦120° C., preferably ≧75° C. to ≦100° C. It is most preferable that terephthalic acid and/or esters of terephthalic acid are used as well, at least proportionally.

The proportion of the terephthalic acid, which is important to the invention, may vary greatly depending on the intended use, and so may be 1–100 mol %, preferably 5–100 mol %, based on all of the carboxylic acids or their esters or anhydrides that are used for preparing the polyester B). These ranges include all specific values and subranges therebetween, such as 2, 8, 10, 15, 20, 25, 30, 40, 50, 60, 75, 80, 85, 90, and 95 mol %.

The polyesters may be obtained conventionally by condensing polyols and polycarboxylic acids in an inert gas atmosphere at temperatures from 100 to 260° C., preferably from 130 to 220° C., in the melt or in an azeotropic regime, as described, for example, in Methoden der Organischen Chemie (Houben-Weyl), Vol. 14/2, 1–5, 21–23, 40–44, Georg Thieme Verlag, Stuttgart, 1963, in C. R. Martens, Alkyd Resins, 51–59, Reinhold Plastics Appl. Series, Reinhold Publishing Comp., New York, 1961 or in DE 27 35 497 and DE 30 04 903, each of which is incorporated herein by reference.

The mixing ratio of polyesters containing hydroxyl groups and terephthalic acid to blocked isocyanate component is generally chosen such that there are from 0.5 to 1.2, preferably from 0.8 to 1.1, with very particular preference 1.0 NCO group(s) per OH group.

For preparing PU powder coated materials the isocyanate component A) is mixed with the suitable polyester B) containing hydroxyl groups and terephthalic acid, and, where appropriate, with customary auxiliaries and additives C). Examples of auxiliaries and additives C) which can be used include catalysts, pigments, fillers, dyes, leveling agents, e.g., silicone oil and liquid acrylic resins, light stabilizers, heat stabilizers, antioxidants, glass enhancers, and effect additives. Components A), B) and C) are homogenized in the melt. This can be done in appropriate apparatus, such as in heatable kneading units, but preferably by extrusion, in the course of which temperature limits of 130 to 140° C. ought not to be exceeded. After cooling to room temperature and appropriate comminution, the extruded homogenized mass is ground to a ready-to-spray powder. Application of the ready-to-spray powder to suitable substrates can be carried out by the known methods, e.g., electrostatic powder spraying, fluidized-bed sintering or electrostatic fluidized-bed sintering. Following powder application, the coated workpieces are cured conventionally by heating in an oven at a temperature of from 160 to 250° C. for from 60 minutes to 30 seconds, preferably at from 170 to 240° C. for from 30 minutes to 1 minute. When using a coil coating oven, the curing conditions are commonly from 200 to 350° C. for from 90 to 10 seconds.

In order to increase the gelling speed of the heat-curable powder coating materials, catalysts can be added. Examples of catalysts used include organotin compounds such as dibutyltin dilaurate, tin(II) octoate, dibutyltin maleate or butyltin tris(2-ethylhexanoate). The amount of catalyst added is from 0.01 to 1.0% by weight, based on the total amount of powder coating material.

With the coating composition used in accordance with the invention it is possible to produce extremely flexible, overbakeable, and weathering-stable PU powder coatings and coil powder coatings.

EXAMPLES

Having generally described this invention, a further understanding can be obtained by reference to certain specific examples which are provided herein for purposes of illustration only and are not intended to be limiting unless otherwise specified.

A) Preparation of $\epsilon$-caprolactam-Blocked Isocyanate Components

Example 1

699.8 g of Desmodur N 3300 (polyisocyanato isocyanurate based on hexamethylene diisocyanate, from Bayer) and 1 632.8 g of VESTANAT T 1890 (polyisocyanato isocyanurate based on isophorone diisocyanate, from Degussa) were heated to 100° C. 3.5 g of dibutyltin dilaurate were added. Subsequently, 1 163.9 g of $\epsilon$-caprolactam were added in portions. An hour after the final portion of $\epsilon$-caprolactam, the reaction was ended. Thereafter, the reaction mixture was cooled to room temperature. The reaction product had a free NCO group content of 0.4%, a total NCO content of 12.0%, and a melting range of 88–91° C.

Example 2 (Comparative)

488.4 g of isophorone diisocyanate were heated to 110° C. with stirring and 68.3 g of monoethylene glycol were metered in. After a reaction time of 60 minutes, 249.1 g of $\epsilon$-caprolactam were added. After a further 60 minutes, the product was cooled and comminuted. The reaction product had a free NCO group content of 0.2%, a blocked NCO group content of 11.4%, and a melting range of 65–75° C.

B) Polyester

A polyester of the following composition was used: as the acid component: 100 mol % dimethyl terephthalate; as alcohol components: 57.5 mol % monoethylene glycol, 0.5 mol % hexane-1,6-diol, 38.5 mol % neopentyl glycol and 3.5 mol % glycerol. The polyester had an OH number of 39 mg KOH/g, an acid number of 2.5 mg KOH/g, and a glass transition temperature of 60° C.

C) Polyurethane Powder Coating Materials

General preparation procedure

The comminuted products—blocked polyisocyanate (crosslinker), polyester, leveling agent, devolatilizer, and catalyst masterbatch—are intimately mixed with the white pigment in an edge runner mill and the mixture is then homogenized in an extruder at up to 130° C. After cooling, the extrudate is crushed and ground to a particle size <100 $\mu$m using a pinned-disk mill. The powder thus produced is applied to degreased, iron-phosphated steel panels using an electrostatic powder spraying unit at 60 kV, and the applied coating is baked in a convection dryer or in a coil coating oven.

The formulations contain 30% by weight Kronos 2160 (titanium dioxide from Kronos), 1% by weight Resiflow PV 88 (leveling agent from Worlée-Chemie), 0.5% by weight benzoin (devolatilizer from Merck-Schuchard) and 0.1% by weight dibutyltin dilaurate (catalyst from Crompton Vinyl Additives GmbH). The OH/NCO ratio was 1:1.

TABLE 1

Data of white-pigmented PU powder coatings

| Crosslinker/polyester | A1/B1 | | A2/B1 (comparative) | |
|---|---|---|---|---|
| Baking conditions | 200° C./10 min | 241° C./70 sec | 200° C./10 min | 241° C./70 sec |
| Film thickness ($\mu$m) | 55–65 | 31–44 | 58–65 | 32–44 |

TABLE 1-continued

Data of white-pigmented PU powder coatings

| Crosslinker/polyester | A1/B1 | | A2/B1 (comparative) | |
|---|---|---|---|---|
| Gloss 60° angle | 91 | 90 | 87 | 74–83 |
| Cupping (mm) | >10 | — | >10 | — |
| BI dir./indir. (inch · lb) | >160/>160 | — | 80/20 | — |
| T-bend | — | 0 T | — | 1.5 T |

Key:
Gloss 60° angle = Gardner gloss measurement (ASTM-D 5233)
Cupping = Erichsen cupping (DIN 53 156)
BI dir./indir. = direct and indirect ball impact (ASTM D 2794-93)
T-bend = deformation test (ECCA T 7)

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 101 59 768.1, filed on Dec. 5, 2001, and incorporated herein by reference in its entirety.

What is claimed is:

1. A process for coating metal coils, comprising:
   coil coating a metal coil with a polyurethane powder coating material which is the reaction product of
   A) an isocyanate component which is totally or partly blocked with ε-caprolactam and comprises a physical mixture of individual isocyanato isocyanurates of aliphatic and (cyclo)aliphatic and/or cycloaliphatic diisocyanates, and
   B) one or more polyesters comprising hydroxyl groups and terephthalic acid, and
      wherein there are 0.5–1.2 NCO groups of A) per OH group of B).

2. The process of claim 1, wherein the coating material further comprises C) one or more customary auxiliaries and/or additives.

3. The process of claim 2, wherein one or more catalysts, pigments, fillers, dyes, leveling agents, light stabilizers, heat stabilizers, antioxidants, gloss enhancers and or effect additives are present as component C).

4. The process of claim 1, wherein the isocyanate component comprises at least one of hexamethylene diisocyanate, 2-methylpentamethylene 1,5-diisocyanate, 2-ethyltetramethylene 1,4-diisocyanate, trimethylhexamethylene 1,6-diisocyanate, isophorone diisocyanate, 4,4'-diisocyanatodicyclohexylmethane, or norbornane diisocyanate.

5. The process of claim 1, wherein the ratio of the isocyanato isocyanurates of aliphatic diisocyanates to the sum of (cyclo)aliphatic and/or cycloaliphatic diisocyanates is from 70:30% by weight to 30:70% by weight.

6. The process of claim 5, wherein the aliphatic diisocyanates are selected from the group consisting of hexamethylene diisocyanate, 2-methylpentamethylene 1,5-diisocyanate, 2-ethyltetramethylene 1,4-diisocyanate, trimethylhexamethylene 1,6-diisocyanate, and mixtures thereof.

7. The process of claim 5, wherein the (cyclo)aliphatic diisocyanate is isophorone diisocyanate.

8. The process of claim 5, wherein the cycloaliphatic diisocyanates are selected from the group consisting of 4,4'-diisocyanatocyclohexylmethane, norbornane diisocyanate, and a mixture thereof.

9. The process of claim 1, wherein the isocyanate component has a total NCO content of from 8 to 22% by weight.

10. The process of claim 1, wherein the isocyanate component is blocked such that there are 0.5–1.1 mol of ε-caprolactam per NCO equivalent.

11. The process of claim 1, wherein the polyesters B) comprising hydroxyl groups and terephthalic acid have an OH functionality of from 2.0 to 5, an OH number of from 20 to 200 mg KOH/g, a viscosity at 160° C. of <60 000 mP·s, and a melting point ≧700° C. to ≦120° C.

12. The process of claim 1, wherein the proportion of terephthalic acid in the polyester B) is 1–100 mol %, based on all of the carboxylic acids or their esters or anhydrides used for preparing the polyester B).

13. The process of claim 1, wherein the OH/NCO ratio is 1:0.5 to 1.2.

14. The process of claim 1, wherein the OH/NCO ratio is 1:0.8 to 1.1.

15. The process of claim 1, wherein the OH/NCO ratio is 1:1.

16. The process of claim 1, wherein the coating material contains a catalyst in a concentration of from 0.01 to 1.0% by weight, based on the total amount of the material.

17. The process of claim 16, wherein the catalyst comprises an organotin compound in a concentration of from 0.01 to 1.0% by weight, based on the total amount of the material.

18. A coated metal coil produced by the process of claim 1.

19. In a process for coating a metal coil, the improvement comprising the metal coil with a polyurethane powder coating material which is the reaction product of
   A) an isocyanate component which is totally or partly blocked with ε-caprolactam and comprises physical mixtures of individual isocyanato isocyanurates of aliphatic and (cyclo)aliphatic and/or cycloaliphatic diisocyanates, and
   B) one or more polyesters comprising hydroxyl groups and terephthalic acid, and
      wherein there are 0.5–1.2 NCO groups of A) per OH group of B).

* * * * *